(12) United States Patent
Vachon (10) Patent No.: US 6,874,370 B1
(45) Date of Patent: Apr. 5, 2005

(54) FINITE ELEMENT ANALYSIS FATIGUE GAGE

(76) Inventor: Reginald I. Vachon, 1414 Epping Forest Dr., Atlanta, GA (US) 30319

( * ) Notice: Subject to any disclaimer, the term of this patent is extended or adjusted under 35 U.S.C. 154(b) by 0 days.

(21) Appl. No.: 10/890,994

(22) Filed: Jul. 15, 2004

(51) Int. Cl.$^7$ ................................................. G01N 3/32
(52) U.S. Cl. ....................................................... 73/808
(58) Field of Search ......................... 73/760, 788, 800, 73/806, 808, 789

(56) References Cited

U.S. PATENT DOCUMENTS

| | | | |
|---|---|---|---|
| 4,008,960 A | 2/1977 | Reytblatt | |
| 4,288,852 A | 9/1981 | Holland | |
| 4,591,996 A | 5/1986 | Vachon et al. | |
| 4,939,354 A | 7/1990 | Priddy et al. | |
| 4,969,106 A | 11/1990 | Vogel et al. | |
| 5,278,776 A | 1/1994 | Fisher et al. | |
| 5,642,293 A | 6/1997 | Manthey et al. | |
| 6,188,483 B1 * | 2/2001 | Ettemeyer | 356/496 |
| 6,189,386 B1 * | 2/2001 | Chen et al. | 73/800 |
| 6,253,623 B1 * | 7/2001 | Joyce et al. | 73/850 |
| 6,532,805 B1 | 3/2003 | Kokawa et al. | |
| 6,594,381 B2 | 7/2003 | Tsap et al. | |
| 6,631,647 B2 | 10/2003 | Seale | |
| 2001/0040997 A1 | 11/2001 | Tsap et al. | |
| 2004/0036853 A1 | 2/2004 | Vachon et al. | |

FOREIGN PATENT DOCUMENTS

| | | |
|---|---|---|
| EP | 0921371 | 6/1999 |
| JP | 57125803 | 8/1982 |
| JP | 2002267422 | 9/2002 |

OTHER PUBLICATIONS

L. Tsap et al., "Fusion Of Physically-Based Registration And Deformation Modeling For Nonrigid Motion Analysis," *IEEE Transactions On Image Processing*, vol. 10, No. 11, Nov. 2001, pp. 1659–1669.

L. Tsap et al., "Nonrigid Motion Analysis Based On Dynamic Refinement Of Finite Element Models," *IEEE Transactions On Pattern Analysis And Machine Intelligence*, vol. 22, No. 5, May 2000, pp. 526–543.

L. Tsap et al., "A Vision-Based Technique For Objective Assessment Of Burn Scars," *IEEE Transactions On Medical Imaging*, vol. 17, No. 4, Aug. 1998, pp. 620–633.

(Continued)

*Primary Examiner*—Edward Lefkowitz
*Assistant Examiner*—T Miller
(74) *Attorney, Agent, or Firm*—Jacobson Holman PLLC (57) ABSTRACT

Machine vision is used to track nodes on the perimeter of a geometric shape associated with a body undergoing cyclic loading, the geometric shape defining a target. The movement of the nodes is related to calculate strain through principles of Finite Element Analysis. The calculated strain is used to determine fatigue damage in the body based on an equation and data obtained using strain-controlled test methods. A finite element analysis fatigue gage includes (1) a sensor to capture the total image of the target and to output data representing the total image, (2) a computer program for (a) isolating the perimeter of the target using edging algorithms and the data, (b) tracking the movement of perimeter nodes of the target as the body undergoes deformation and recording the displacement, and (c) manipulating the data on movement of the nodes using (i) nonlinear stress analysis, (ii) finite element analysis, and (iii) material properties and characteristics and an equation based on strain-controlled test methods, and (3) a data display.

12 Claims, 3 Drawing Sheets

OTHER PUBLICATIONS

"Application of Data Matrix Identification Symbols to Aerospace Parts Using Direct Part Marking Methods/Techniques," NASA–HDBK–6003, Jul. 2, 2001.

V.V. Novozhilov, *Foundations of The Nonlinear Theory of Elasticity,* Graylock Press, Rochester, NY, 1953, pp. 37–41.

Boresi, Arthur P., Chong Ken P., and Saigal, Sunil, *Approximate Solution Methods in Engineering Mechanics,* Second Edition, John Wiley & Sons, New York, 2003, pp. 1–9.

Stephens, Ralph I., Fatemi Ali, Stephens, Robert R., and Fuchs, Henry O., *Metal Fatigue in Engineering,* Second Edition, John Wiley & Sons, Inc. New York 2001, pp. 93–119.

ASTM International, *Standard Practice for Strain–Controlled Fatigue Testing, Designation E 606–92* (Reapproved 1998) West Conshohocken, PA, pp. 1–15.

* cited by examiner

Reversals to failure, $2N_f$ (log scale)

FINITE ELEMENT ANALYSIS FATIGUE GAGE

CROSS-REFERENCE TO RELATED APPLICATIONS

Not applicable.

COPYRIGHTED MATERIAL

A portion of the disclosure of this patent document contains material which is subject to copyright protection. The copyright owner has no objection to the facsimile reproduction by anyone of the patent document or the patent disclosure, as it appears in the Patent and Trademark Office patent file or records, but otherwise reserves all copyright rights whatsoever.

BACKGROUND OF THE INVENTION

1. Field of the Invention

The present invention relates a method and apparatus for calculating strain and fatigue damage. More specifically, the invention relates to a method and apparatus for calculating strain and fatigue damage in materials based on observing the deformation of a geometric shape associated with (for example by affixing to, identifying on, or embedding in) the body under study, coupled with the use of finite element analysis principles and principles of mechanics of materials.

2. Related Art

There have been many technical efforts made towards measuring and/or calculating strain and determining fatigue damage in materials. "Measuring" as used herein means determining a magnitude with reference to a standard of measurement; and "calculating" as used herein means determining a value using a mathematical model of a physical model of a phenomenon or a phenomenological equation. Examples of such technical efforts are disclosed in U.S. Pat. No. 4,591,996 to Vachon and Ranson, Japanese application No. JP 57125803 for "Method for Measuring Strain of Sample Surfaces," Japanese patent publication No. JP 2002267422 for "Method and Device for Crack Detection," U.S. Pat. No. 4,008,960 for "Photoelastic Strain Gauge Coating and Method of Using Same," European Patent Application No. EP 0 921 371 A2 for "Method of using a Microscopic Digital Strain Gauge." Published U.S. application No. 2004/0036853 of Vachon and Ranson discloses a strain gage that can measure strain directly, as well as assess fatigue damage, using a target comprising a strain rosette in the form of a compressed symbol that is defined in terms of its physical dimensions, and more particularly, of the end points of three intersecting line segments that define the strain rosette.

Technical efforts have continued in the area of optical correlation of surface images to detect strain. Specifically, these efforts include, among other things: (1) optical detection of edges of images on surfaces as well as optical detection of edges of surfaces, (2) optical correlation of dot and other geometric shapes applied to surfaces, and (3) optical correlation of the movement of centroids of geometric shapes applied to surfaces. All of these analytical and experimental efforts have been directed to optical detection of strain.

It is to the solution of these and other problems that the present invention is directed.

SUMMARY OF THE INVENTION

Definitions and abbreviations are used herein as follows:

Fatigue damage (also sometimes referred to as accumulated damage)—the cumulative or irreversible damage incurred in materials caused by cyclic application of stresses and environments resulting in degradation of load carrying capacity.

Data matrix symbol—a type of two-dimensional matrix code containing dark and light square data modules. It is designed to pack a lot of information in a very small space; a Data Matrix symbol can store between one and 3116 numeric or 2335 alphanumeric characters. A Data Matrix symbol has a finder pattern of two solid lines and two alternating dark and light lines on the perimeter of the symbol. These patterns are used to indicate both orientation and printing density of the symbol. A two-dimensional imaging device such as a CCD camera is used to scan the symbology.

The information in a Data Matrix symbol is encoded by absolute dot position rather than relative dot position. While a Data Matrix symbol is easily scalable between a 1-mil square to a 14-inch square, the actual limits are dependent on the fidelity of the marking device and the optics of the sensor. Data Matrix symbols can be used for small item marking applications using a wide variety of printing and marking technologies.

Additional information regarding Data Matrix code is disclosed in U.S. Pat. Nos. 4,939,354; 5,053,609; and 5,124, 536; see also "Application of Data Matrix Identification Symbols to Aerospace Parts Using Direct Part Marking Methods/Techniques," NASA-HDBK-6003, Jul. 2, 2001.

Node—in Finite Element Analysis, the points within the elements where the degrees of freedom (variables) are defined.

It is a primary object of the present invention to provide a method and apparatus for calculating strain and fatigue damage in materials based on the principles of Finite Element Analysis.

The present invention involves using machine vision to track nodes on the perimeter of a geometric shape associated with (for example, by affixing to or identifying on or forming in the surface of a body undergoing cyclic loading, the geometric shape defining a target; relating the movement of the nodes of the target on or in the body to calculate strain through principles of Finite Element Analysis; and then using the calculated strain to determine fatigue damage in the body based on an equation and data obtained using strain-controlled test methods of the type described in Stephens, Ralph I., Fatemi Ali, Stephens, Robert R., and Fuchs, Henry O., *Metal Fatigue in Engineering*, Second Edition, John Wiley & Sons, Inc. New York 2001 (hereafter, "Stephens et al.").

The finite element analysis fatigue gage in accordance with the present invention comprises (1) a sensor (for example, a camera) to capture the total image of the target and to output data representing the total image of the target, (2) a computer program for (a) isolating the perimeter of the target using edging algorithms and the data acquired from the sensor, (b) tracking, relative to a coordinate system and as a function of time, the movement of perimeter nodes of the target as the body undergoes deformation during or after the termination of cyclic loading, and recording the displacement as a function of time, and (c) manipulating the data on movement of the nodes using (i) fundamental concepts of nonlinear stress analysis as developed by V. V.

Novozhilov, *Foundations of The Nonlinear Theory of Elasticity*, Graylock Press, Rochester, N.Y., 1953 (hereafter, "Novozhilov"), (ii) finite element analysis (see Boresi, Arthur P., and Saigal, Sunil, *Approximate Solution Methods in Engineering Mechanics*, Second Edition, John Wiley & Sons, New York, 2003 (hereafter, "Boresi et al."), for a description of the principles of finite element analysis), and (iii) material properties and characteristics and an equation based on strain-controlled test methods (as described by Stephens et al. or any new or other approach to describe total strain in terms of elastic and plastic strain and monotonic and cyclic properties), and (3) means for displaying manipulated data.

The method for calculating strain and fatigue damage in materials in accordance with the present invention comprises the steps of:

1. Associating (for example, by affixing or forming or identifying) a geometric shape on the surface of, or internally to, a body to be subjected to cyclic loading, the geometric shape defining a target;
2. Using a sensor (operating in any portion of the electromagnetic spectrum, a magnetic field, or acoustic spectrum) to observe the surface and the target and output data;
3. Using a computer program to isolate the perimeter of the target based on data obtained from the sensor;
4. Inputting to a computer program the mechanical properties of the body (monotonic and cyclic);
5. Using the computer program to set the number of nodes to be tracked and establishing the nodes on the perimeter of the target in accordance with finite element theory;
6. Tracking, relative to a coordinate system and as a function of time, the movement of perimeter nodes of the target as the body undergoes deformation during or after the termination of cyclic loading, and recording the displacement as a function of time, using the computer program;
7. Utilizing the data on movement of nodes in finite element equations to calculate total strain, and then substituting the calculated total strain into an equation developed for strain as a function of monotonic and cyclic properties and reversals (as described by Stephens et al., or any modification, improvement, or update to the equation described by Stephens et al., or any new or other approach to describe total strain in terms of elastic and plastic strain and monotonic and cyclic properties) to calculate fatigue damage as a function of the local total strain.

Other objects, features and advantages of the present invention will be apparent to those skilled in the art upon a reading of this specification including the accompanying drawings.

BRIEF DESCRIPTION OF THE DRAWINGS

The invention is better understood by reading the following Detailed Description of the Preferred Embodiments with reference to the accompanying drawing figures, in which like reference numerals refer to like elements throughout, and in which.

DETAILED DESCRIPTION OF THE PREFERRED EMBODIMENTS

In describing preferred embodiments of the present invention illustrated in the drawings, specific terminology is employed for the sake of clarity. However, the invention is not intended to be limited to the specific terminology so selected, and it is to be understood that each specific element includes all technical equivalents that operate in a similar manner to accomplish a similar purpose.

The present invention is described below with reference to flowchart illustrations of methods, apparatus (systems) and computer program products according to an embodiment of the invention. It will be understood that at least some of the blocks of the flowchart illustrations, and combinations of blocks in the flowchart illustrations, can be implemented by computer program instructions. These computer program instructions may be provided to a processor of a general purpose computer, special purpose computer, or other programmable data processing apparatus to produce a machine, such that the instructions, which execute via the processor of the computer or other programmable data processing apparatus, create means for implementing the functions specified in the flowchart block or blocks.

These computer program instructions may also be stored in a computer-readable memory that can direct a computer or other programmable data processing apparatus to function in a particular manner, such that the instructions stored in the computer-readable memory produce an article of manufacture including instruction means which implement the function specified in the flowchart block or blocks.

The computer program instructions may also be loaded onto a computer or other programmable data processing apparatus to cause a series of operational steps to be performed on the computer or other programmable apparatus to produce a computer implemented process such that the instructions which execute on the computer or other programmable apparatus provide steps for implementing the functions specified in the flowchart block or blocks.

The present invention is based on the results from mechanics of materials fundamentals, which when combined, yield fatigue damage. These mechanics of materials fundamentals are (1) deformation in the neighborhood of an arbitrary point on a body, (2) finite element analysis, and (3) fatigue damage related to plastic strain.

In accordance with the present invention, a geometric shape with an external boundary is applied directly or indirectly to the surface of a body for which strain is to be calculated, or is identified to define a target. A geometric shape can be identified by observing naturally occurring patterns or objects that define a pattern on a macroscopic or microscopic scale. Whether applied or identified, the target can be covered by paint or other material, or it can be embedded in the object for which strain is to be measured.

In one embodiment of the invention, the shape can be defined by a linear or "two dimensional bar code," particularly a Data Matrix symbol.

In another embodiment of the invention, the shape can be identified in a pre-existing overall image.

There are an infinite number of image configurations for the target. The target can be composed of a plurality of sub-images, each of which can be assigned nodes on the perimeters of the sub-images, and can be monitored by the sensor to correlate the movement of the nodes of the sub-images or an image composed of the sub-images may be used and the nodes on the perimeter of the image can be used.

The specific target must be associated with an object (by application or identification) in such a way that the deformation of the target and the deformation under load of the object with which it is associated (that is, to which it is applied or on which it is identified) bear a one-to-one relationship. The target can naturally emit a detectable physical quantity (as, for example, a material that naturally emits a magnetic field), emit a detectable physical quantity upon external stimulation (as, for example, a material that creates a magnetic field when subjected to a current or a material that emits light when stimulated by an electric field), or reflect a detectable physical quantity; and the physical quantity can be a signal in any bandwidth of the electromagnetic spectrum (including the audio frequency range, i.e., the acoustic spectrum), or it can be a field such as a magnetic field.

The detectable physical quantity can be a signal in any portion of the electromagnetic spectrum (including the audio frequency range, i.e., the acoustic spectrum), or it can be a field such as a magnetic field. In the case of a target that can be monitored optically, such as a target incorporated into a Data Matrix symbol, the input signal to the sensor may be a grayscale image that can be converted into a bitmap file, although other inputs can be accommodated.

The target is scalable, in that it can be produced and sensed on a scale ranging from microscopic to macroscopic. Thus, the finite element fatigue gage in accordance with the present invention is applicable to very large applications, such as viewing a target on earth's surface from space to calculate one or both of surface and subsurface strains. All that is required is to match the sensor to the size of the target image and the detectable physical quantity emitted by the target.

The finite element analysis fatigue gage in accordance with the present invention comprises (1) a sensor (for example, a camera) to capture the total image of the target and to output data representing the total image of the target, (2) a computer program for (a) isolating the perimeter of the target using edging algorithms and the data acquired from the sensor, (b) tracking, relative to a coordinate system and as a function of time, the movement of perimeter nodes of the target as the body undergoes deformation during or after the termination of cyclic loading, and recording the displacement as a function of time, and (c) manipulating the data on movement of the nodes using (i) fundamental concepts of nonlinear stress analysis as developed by Novozhilov, (ii) finite element analysis (see Boresi, for a description of the principles of finite element analysis), and (iii) material properties and characteristics and an equation based on strain-controlled test methods (as described by Stephens et al.), and (3) means for displaying manipulated data.

The sensor observes the deformation of the target, if any, over time. The sensor can be an optical, magnetic, electromagnetic, acoustic, or other sensor, as appropriate. Sensors that will sense various detectable physical quantities, including all these signals and fields, are commercially available. The sensor is selected to be compatible with the detectable physical quantity emitted or reflected by the target and undertakes some pre-processing of the observed physical quantity to provide data representing the physical quantity to a computer. Observation can take place on a continuous basis, at random times triggered by an external event, or at pre-determined intervals.

The computer implements programs that identify (assign) the nodes, correlate the specific sub-images used to detect the movement of the nodes, quantify the movements of the nodes to determine their displacement and thereby the distortion of the target, and utilize the data obtained as input for strain equations based on finite element analysis as described herein to yield and display strain in two dimensions in real time and ultimately calculate fatigue damage by substituting the calculated total strain into an equation developed for strain as a function of monotonic and cyclic properties and reversals (as described by Stephens et al. or any modification, improvement, or update to the equation described by Stephens et al. or any new or other approach to describe total strain in terms of elastic and plastic strain and monotonic and cyclic properties.). The technology is scalable with respect to the size of the object under study.

Examples of application of a target include, but are not limited to:

1. Application to a medium such as a polymide film that is bonded, for example by gluing, to the surface of the object for which strain is to be measured (indirect application);
2. Etching on a surface (direct application);
3. Painting on surface (direct application); and
4. Printing on a surface (direct application).

Target applications are described in detail in NASA STD 6002 and Handbook 6003.

Examples of identification of a target include, but are not limited to:

1. Identification by observing naturally-occurring surface features of the object that define a geometric shape with a perimeter on a macroscopic or microscopic scale (for example, features on the surface of the earth or microscopic features on biological, organic, and inorganic materials.).
2. Identification by observing naturally-occurring subsurface features of the object that define a geometric shape with a perimeter on a macroscopic or microscopic scale (for example, a fossil buried in the earth).
3. Identification by observing manmade surface features of the object that define a geometric shape with a perimeter on a macroscopic or microscopic scale (for example, a collection of components).
4. Identification by observing manmade subsurface features of the object that define a geometric shape with a perimeter on a macroscopic or microscopic scale (for example, structural elements of a spacecraft covered with a skin, the structural elements of a bridge covered with a skin, or the structural elements of a building having a surface opaque in the visible spectrum).

Examples of embedding of a target include, but are not limited to:

1. Embedding in the object to be studied when the object is being formed;
2. Identification of naturally occurring or manufactured subsurface features;

3. Covering with an overlying material, such as one or more layers of paint; and
4. Implanting in a human body, in a body part, or an implant. For example, if the target is affixed to a critical area of a hip joint or a hip implant, or to an artificial heart valve, the target can be viewed through the tissue surrounding the target by an x-ray sensor, and the strain and fatigue damage to the associated body part or implant can be assessed over time.

The finite element analysis fatigue gage in accordance with the present invention can be used in the assessment of fatigue damage (accumulation) in critical areas of structures or components of devices subjected to cyclic or other loadings. This is accomplished by observing the area of a component under study over a selected period of time during the normal usage of the area. The data can then be used to predict failure of the component.

The equations set forth by Novozhilov to describe the deformation in the neighborhood of an arbitrary point of a body can be used to derive approximating polynomials, discussed hereinafter, to describe strain in terms of displacements. Specifically, this derivation of the polynomials allows the determination of $\epsilon_{xx}$, $\epsilon_{yy}$, $\epsilon_{xy}$, which are expressed by Finite Element Analysis principles, which permit calculation of total strain as described below.

Finite element analysis (Boresi et al.) is then used to designate nodes: (corresponding to the coefficients in the approximating polynomials for displacements) on the perimeter of a geometric symbol associated with the undeformed body to be subjected to cyclic loadings. As indicated in Equation (28) and Equation (29), the perimeter nodes correspond to the number of coefficients in the approximating polynomials. Tracking the perimeter nodes and using Finite Element Analysis permits calculation of strain, the "measured strain." The number of nodes selected to be tracked on the perimeter of the target directly affects the accuracy of the values of strain.

Fatigue and plastic strain are related. As described below, an equation is derived that relates plastic strain to "reversals" (also referred to as "cycles") of cyclic loadings and the monotonic and cyclic properties of the material. Materials are subjected to cyclic loading to yield monotonic and cyclic properties, in accordance with practices such as, but not limited to, ASTM International, *Standard Practice for Strain-Controlled Fatigue Testing*, Designation E 606-92 (Reapproved 1998) West Conshohocken, Pa. (hereafter, "ASTM E 606-92"). The derivation is material invariant as the theory is applicable to all materials.

The "measured strain" using Finite Element Analysis is equated to the equation that relates plastic strain to reversals, which contains one unknown, the number of "reversals" at any instant of time corresponding to a "measured strain". The ratio of the number of reversals for a "measured strain" to the known reversals to failure gives the state of fatigue in the material.

Figure 1:
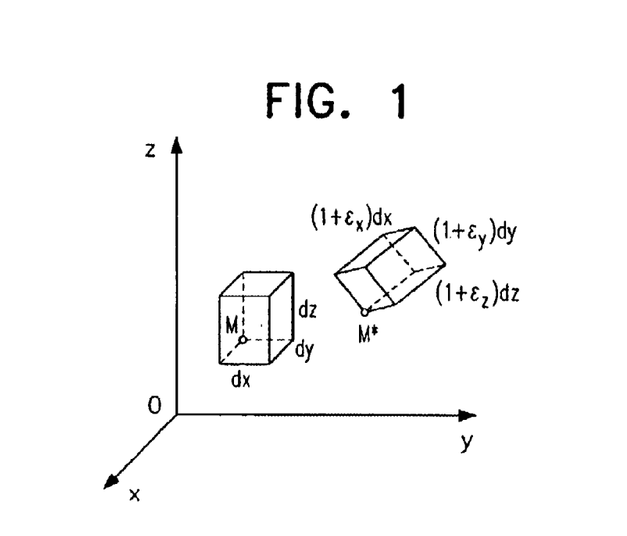
FIG. 1 illustrates the transformation, under deformation, of an infinitesimal parallelepiped in a body into a parallelepiped with different dimensions and with different angles between the sides.

As set forth by Novizhilov, analytical geometry has established that affine transformations preserve straight lines, planes, and parallelism of straight lines. Moreover, affine transformations preserve quadric surfaces. For example, a sphere is transformed into an ellipsoid. Further, under deformation, every solid that, before transformation, is an infinitesimal parallelepiped becomes a parallelepiped with different dimensions and with different angles between the sides. This is illustrated in FIG. 1.

Figure 2:
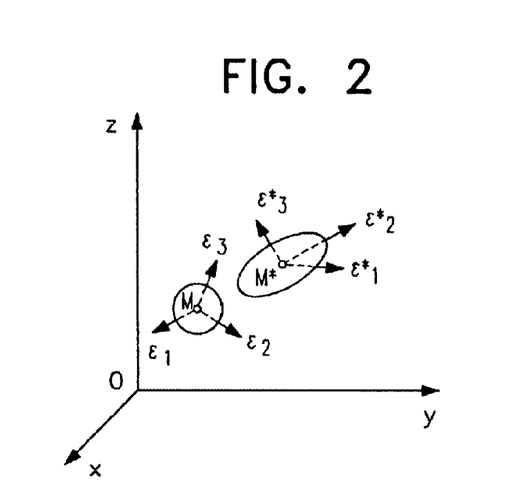
FIG. 2 illustrates the transformation, under deformation, of a sphere into an ellipsoid.

The points that lie on a sphere before deformation lie on an ellipsoid after deformation, as shown in FIG. 2. The direction of the axes of the ellipsoid corresponds to the principal axes of strain, because the extremal values correspond to the semi-axis of the ellipsoid. As a special case, if the points lie on the surface of a continuum, then a rectangle deforms into a parallelogram and a circle deforms into an ellipse. Thus, it is possible to calculate strain using the movement of node points on the perimeter of rectangular, square, circular or curvilinear target associated with (for example, affixed to) the surface of a body undergoing deformation to calculate strain, and then to use the resulting strain calculation to determine fatigue damage using the results in Equation (28).

Figure 3:
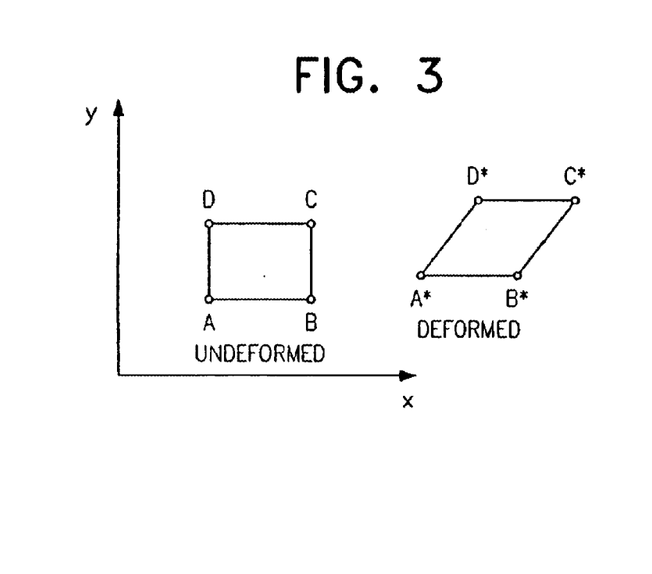
FIG. 3 illustrates the deformation of a square on the surface into a parallelogram.

The determination of strain using the above-described technique is explained as follows for a square. Similar results can be obtained for other geometric shapes. Consider a square on the surface of a body, which square deforms with a load on the body into a parallelogram as shown in FIG. 3. Corner points A, B, C, and D of the un-deformed square deform into corner points A*, B*, C*, and D* of the deformed parallelogram. A*, B*, C*, D* completely characterize the deformation (strains) of the region surrounded by points A, B, C, D.

Figure 4:
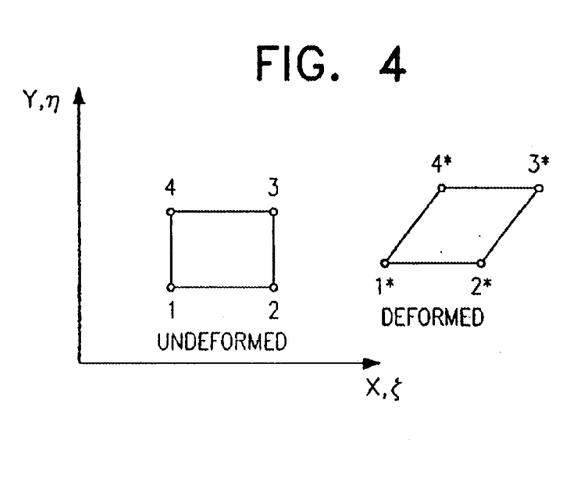
FIG. 4 illustrates the definition of coordinate relationships for both the undeformed and deformed element.

Assume points A, B, C, D are initially parallel to the X-Y coordinate axes as illustrated in FIG. 3. FIG. 4 defines coordinate relationships in the following development for both the undeformed and deformed element.

Coordinates that describe the corner points before deformation are denoted as:

1: $X_1$, $Y_1$
2: $X_2$, $Y_2$
3: $X_3$, $Y_3$
4: $X_4$, $Y_4$

Coordinates that describe these same points in the deformed configuration are:

1*: $\delta_1$, $\eta_1$
2*: $\delta_2$, $\eta_2$
3*: $\delta_3$, $\eta_3$
4*: $\delta_4$, $\eta_4$ The relationship between the deformed and undeformed coordinates are described by Novozhilov in terms of displacement functions as:

$$\zeta = X + u(X, Y) \qquad \text{Eq. (1)}$$

$$\eta = Y30 \, v(X, Y) \qquad \text{Eq. (2)}$$

A fundamental approximation used in the finite element analysis fatigue gage in accordance with the present invention is that the measured displacement (u, v) at any point P in the element is interpolated from the node displacements using interpolating polynomials. The order of the polynomial depends on the number of measured nodes in the element. The general form of an interpolation polynomial is written for each displacement as:

$$u = C_0 + C_1 X + C_2 Y + C_3 XY + C_4 X_2 + C_5 Y_2 + \qquad \text{Eq. (3)}$$

$$v = D_0 + D_1 X + D_2 Y + D_3 XY + D_4 X_2 + D_5 Y_2 + \qquad \text{Eq. (4)}$$

where the constants $C_0$ through $C_5$ and $D_0$ through $D_5$ are evaluated from the measured nodal values of the finite element analysis fatigue gage. The polynomial coefficients $C_i$ and $D_i$ are constants and are sometimes called generalized displacement coordinates.

Two examples, discussed below, are used to illustrate the application of the finite element analysis fatigue gage in accordance with the present invention, (1) the "constant strain triangle" and (2) the "bilinear strain rectangle."

For a constant strain triangle, the general form of an interpolation polynomial is written for each displacement as:

$$\zeta = X + C_0 + C_1 X + C_2 Y \quad \text{Eq. (5)}$$

$$\eta = Y + D_0 + D_1 X + D_2 Y \quad \text{Eq. (6)}$$

Three nodes are needed to determine the generalized coordinates:

$$\zeta_1 = X_1 + C_0 + C_1 X_1 + C_2 Y_1 \quad \text{Eq. (7)}$$

$$\zeta_2 = X_2 + C_0 + C_1 X_2 + C_2 Y_2 \quad \text{Eq. (8)}$$

$$\zeta_3 = X_3 + C_0 + C_1 X_3 + C_2 Y_3 \quad \text{Eq. (9)}$$

Assign local coordinates:

$$\zeta_1 = Y_1 \quad \text{Eq. (10)}$$

$$X_1 = Y_1 = 0 \quad \text{Eq. (11)}$$

such that $C_0$ and $D_0$ are zero (rigid body terms). The terms $C_1$, $C_2$, $D_1$, $D_2$ can be solved from Equation (12):

$$\begin{vmatrix} \zeta_2 - X_2 \\ \zeta_3 - X_3 \end{vmatrix} = \begin{vmatrix} X_2 & Y_2 \\ X_3 & Y_3 \end{vmatrix} \begin{vmatrix} C_1 \\ C_2 \end{vmatrix} \quad \text{Eq. (12)}$$

All quantities in this equation are either measured or assigned; therefore $C_1$ and $C_2$ are the unknown values. The solution is based on standard mathematical methods.

In a similar manner, the constants $D_2$ and $D_3$ are computed from Equation (13):

$$\begin{vmatrix} \eta_2 - Y_2 \\ \eta_3 - Y_3 \end{vmatrix} = \begin{vmatrix} X_2 & Y_2 \\ X_3 & Y_3 \end{vmatrix} \begin{vmatrix} D_1 \\ D_2 \end{vmatrix} \quad \text{Eq. (13)}$$

where the local coordinates are assigned $$\eta_1 = Y_1, \quad \text{Eq. (14)}$$

$$X_1 = Y_1 = 0 \quad \text{Eq. (15)}$$

The constant strain triangle is the simplest element that can be used. Other elements are used that are based on different interpolation functions that often yield better results than those obtained using the constant strain triangle. The number of alternatives is large. The bilinear rectangle is presented as another example to illustrate the procedure. Four constants are needed in the interpolation function for the bilinear rectangle:

$$\zeta_1 = X_1 + C_0 + C_1 X_1 + C_2 Y_1 + C_3 X_1 Y_1 \quad \text{Eq. (16)}$$

$$\zeta_2 = X_2 + C_0 + C_1 X_2 + C_2 Y_2 + C_3 X_2 Y_2 \quad \text{Eq. (17)}$$

$$\zeta_3 = X_1 + C_0 + C_1 X_3 + C_2 Y_3 + C_3 X_3 Y_3 \quad \text{Eq. (18)}$$

$$\zeta_4 = X_4 + C_0 + C_1 X_4 + C_2 Y_4 + C_3 X_4 Y_4 \quad \text{Eq. (19)}$$

Following the same procedure as in the constant strain triangle, unknowns $C_1$, $C_2$, $C_3$ can be solved from Equation (20):

$$\begin{vmatrix} \zeta_2 - X_2 \\ \zeta_3 - X_3 \\ \zeta_4 - X_4 \end{vmatrix} = \begin{vmatrix} X_2 & Y_2 & X_2 Y_2 \\ X_3 & Y_3 & X_3 Y_3 \\ X_4 & Y_4 & X_4 Y_4 \end{vmatrix} \begin{vmatrix} C_1 \\ C_2 \\ C_3 \end{vmatrix} \quad \text{Eq. (20)}$$

Constants $D_1$, $D_2$, $D_3$ can be determined by solving Equation (21):

$$\begin{vmatrix} \eta_2 - y_2 \\ \eta_3 - Y_3 \\ \eta_4 - Y_4 \end{vmatrix} = \begin{vmatrix} X_2 & Y_2 & X_2 Y_2 \\ X_3 & Y_3 & X_3 Y_3 \\ X_4 & Y_4 & X_4 Y_4 \end{vmatrix} \begin{vmatrix} D_1 \\ D_2 \\ D_3 \end{vmatrix} \quad \text{Eq. (21)}$$

Strain components are calculated from the theory of elasticity as found in Novozhilov. The strains are tabulated for the bilinear rectangle as follows:

$$\varepsilon_{xx} = \frac{\partial u}{\partial x} + \frac{1}{2}\left[\left(\frac{\partial u}{\partial x}\right)^2 + \left(\frac{\partial v}{\partial x}\right)^2\right] \quad \text{Eq. (22)}$$

$$\epsilon_{xx} = C_1 + C_3 Y + \frac{1}{2}[(C_1 + C_3 Y)^2 + (D_1 + D_3 Y)^2] \quad \text{Eq. (23)}$$

$$\varepsilon_{yy} = \frac{\partial v}{\partial y} + \frac{1}{2}\left[\left(\frac{\partial u}{\partial y}\right)^2 + \left(\frac{\partial v}{\partial y}\right)^2\right] \quad \text{Eq. (24)}$$

$$\epsilon_{yy} = D_2 + D_3 Y + \frac{1}{2}[(C_2 + C_3 X)^2 + (D_2 + D_3 X)^2] \quad \text{Eq. (25)}$$

$$\varepsilon_{xy} = \frac{\partial v}{\partial y} + \frac{1}{2}\left[\left(\frac{\partial u}{\partial y}\right)^2 + \left(\frac{\partial v}{\partial y}\right)^2\right] \quad \text{Eq. (26)}$$

$$\epsilon_{xy} = C_2 + C_3 X + D_1 + D_3 Y + (C_1 + C_3 Y)(C_2 + C_3 X) + (D_1 + D_3 Y)(D_2 + D_3 X) \quad \text{Eq. (27)}$$

The explanation herein of the technical basis of the present invention utilizes a Cartesian coordinate system and specific shapes for illustration. However, any coordinate system and any geometric shape can be used as long as the coordinate system is consistent for the shape of the target and analyses of the strain equations, because Novozhilov shows that affine transformations preserve quadric surfaces.

An important aspect of the fatigue process is plastic deformation. As explained by Stephens et al., fatigue cracks usually nucleate from plastic strains in localized regions. Most fatigue failures begin at local discontinuities where local plasticity exists and crack nucleation and growth are governed by local plasticity at the crack tip.

Fatigue damage is assessed directly in terms of local strain, which is called the "local strain approach" (see Stephens et al.). A reasonable expected fatigue life, based on the nucleation or formation of small macro-cracks in a body can then be determined, if one knows the local strain-time history at a notch in the body and the un-notched strain-life fatigue properties of the material from which the body is made.

The conclusions from these facts presented by Stephens et al are:

1) Fatigue damage is a function of plasticity;
2) Fatigue damage is assessed in terms of local plastic strain.
3) A strain-based approach to fatigue unifies the treatment of low-cycle and high-cycle fatigue (see Stephens et al.).
4) This approach also applies to long-life applications where small plastic strains may exist;
5) The ability to monitor local plastic strains permits the measurement of fatigue damage. This measurement is the most effective when it occurs during crack nucleation prior to the formation of detectable cracks in the material; and 6) Stephens et al. state that failure criteria for strain-life curves (depicted in FIG. 5) have not been consistently defined in that failure may be life to a small detectable crack, life to a certain percentage decrease in tensile load, life to certain decrease to the ratio of unloading to loading moduli, or life to fracture. ASTM E 606-92 defines failure as a tensile load drop of 50 percent, which is before crack initiation. The finite element analysis strain gage in accordance with the present invention allows fatigue damage to be defined based on whatever definition is used for failure. The important fact is the finite element analysis strain gage allows the calculation of fatigue damage prior to crack initiation based on the selection of the definition of failure prior to cracking or fracture.

Stephens et al and ASTME E 606-92 present the derivation of the following equation for the total strain-life equation:

$$\varepsilon_{Total} = \sigma'_f / E(2N_f)^b + \varepsilon'_f(2N_f)^c \qquad \text{Eq. (28)}$$

Figure 5:
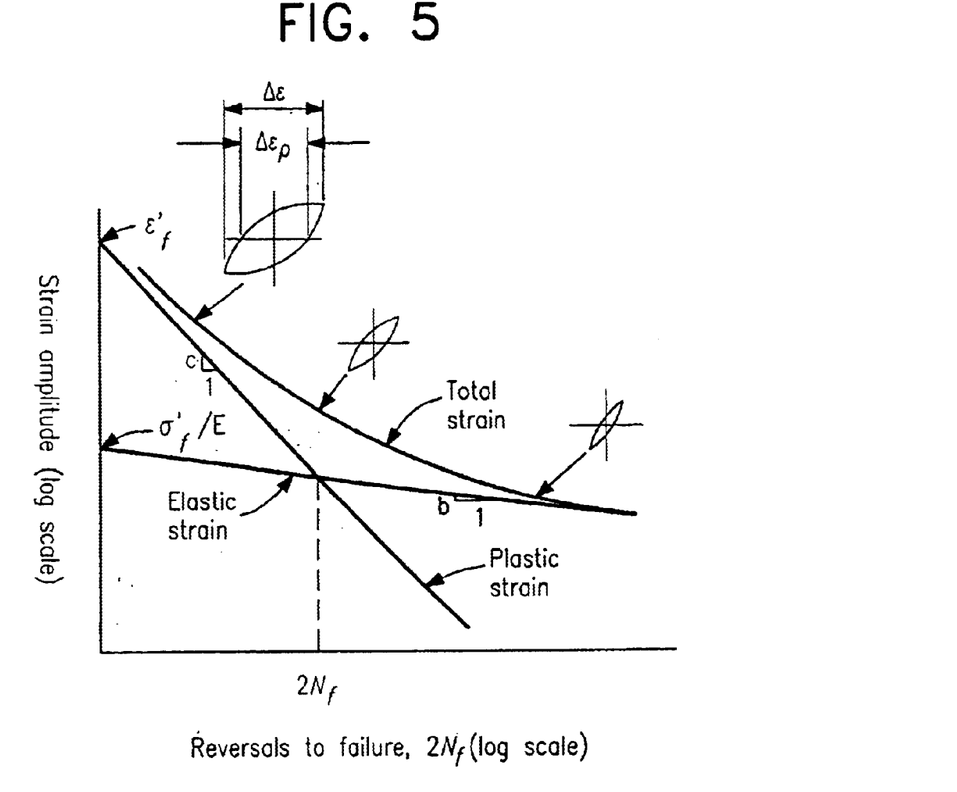
FIG. 5 illustrates failure criteria for strain-life curves (more specifically, a log—log plot of Strain Amplitude versus Reversals to Failure, $2N_f$).

The applicability of Equation (28) to the instant invention is understood by considering the following. The components of strain are plastic and elastic, as illustrated by FIG. 5. FIG. 5 is a log—log plot of Strain Amplitude versus Reversals to Failure, $2N_f$, where:

| | | |
|---|---|---|
| $\Delta\varepsilon/2$ = total strain amplitude = | $\varepsilon_a$ | |
| $\Delta\varepsilon_e/2$ = elastic strain amplitude = | $\Delta\sigma/2E$ = | $\sigma_a/E$ |
| $\Delta\varepsilon_p/2$ = plastic strain amplitude = | $\Delta\varepsilon/2 - \Delta\varepsilon_e/2$ | |
| $\varepsilon$ = fatigue ductility coefficient | | |
| c = fatigue ductility exponent | | |
| $\sigma'_f$ = fatigue strength coefficient | | |
| b = fatigue strength exponent | | |
| E = modulus of elasticity | | |
| $\Delta\sigma/2E$ = stress amplitude = | $\sigma$ | |

Figure 6:
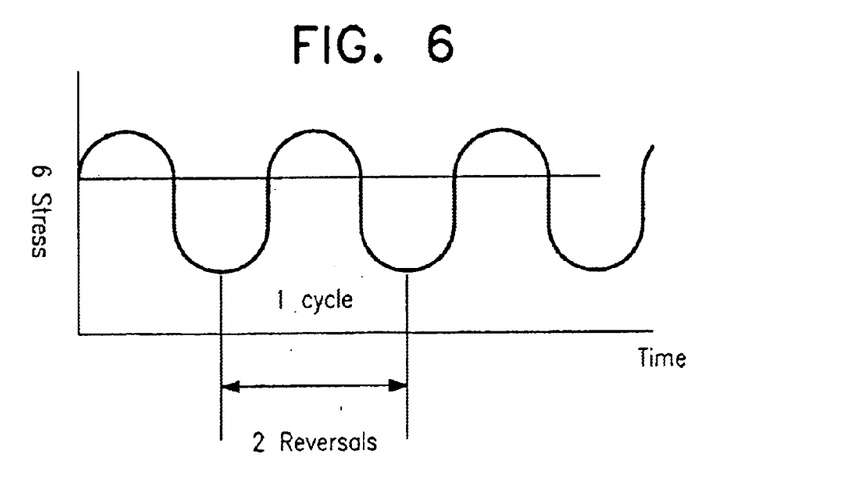
FIG. 6 illustrates the number of reversals in one cycle in constant amplitude loading and the number of reversals in a defined cycle in variable amplitude loading.

FIG. 6 defines reversals and cycles to failure as used in strain-controlled tests of material specimens subjected to cyclic loading (see ASTM E 606-92). FIG. 6 further illustrates that one cycle equals two reversals in constant amplitude loading, and that in variable amplitude loading, a defined cycle may contain a number of reversals. The preceding paragraph and ASTM E 606-92 define the terms in Equation (28). The terms defined in the preceding paragraph are used in Equation (28) to generate the data to define the curves in FIG. 5. Further, use of ASTM E 606-92 yields the exponents, coefficients and reversals to failure for a particular material. Moreover, Equation (28) can be used to determine the number of reversals prior to failure. If the total strain at any instant of time is known prior to failure, the reversals $N_f$, for that strain at that instant of time can be calculated using the coefficients and exponents for the material under study. The ratio of the reversals at any instant of time to reversals to failure is an indication of fatigue damage, or one can write $$\text{Fatigue damage} = \frac{N_f \text{ corresponding to strain calculated prior to failure at any instant of time}}{N_f \text{ at failure as illustrated in Figure 5}} \qquad \text{Eq. (29)}$$

Fatigue damage can now be determined by using the results obtained from tracking the nodes on the perimeter of the target to calculate total strain and using Equation (28) with coefficients and exponents and data from tables for materials subjected to ASTM E 606-92 to obtain $N_f$ prior to failure and dividing that by $N_f$ at failure. The ratio is the fatigue damage. Determination of the fatigue damage from the ratio forms the basis on which the fatigue gage in accordance with the present invention operates. It should be noted that ASTM E 606-92 may not be the only method for generating data for Equation (28). Other practices that provide coefficients and exponents and data for materials subjected thereto may also be used.

In another embodiment of the invention, the shape can be identified in a pre-existing overall image.

One advantage of the finite element analysis fatigue gage in accordance with the present invention is that strain is calculated using finite element analysis principles directly. This in turn leads to greater accuracy and reduced system errors.

Another advantage of the finite element analysis fatigue gage in accordance with the present invention is that the range of strain measurements is easily from 0 to at least 50%, which permits measurements of strain in elastic materials such as rubber and plastic. The potential exits to cover measurements at the nanoscale level.

A third, and major advantage of the finite element analysis fatigue gage in accordance with the present invention is that subsurface strains can be measured. Subsurface measurements can have special applications in man-made composites.

The finite element analysis fatigue gage in accordance with the present invention can be used in the assessment of fatigue damage (accumulation) in critical areas of structures or components of devices subjected to cyclic or other loadings. This is accomplished by observing the area of a component under study over a selected period of time during the normal usage of the area. The data can then be used to predict failure of the component.

The method in accordance with the present invention employs correlation of the nodes on the perimeter of sub-images as would be associated with a two-dimensional bar code or the correlation of identified sub-images in a symbol with a defined or identifiable perimeter applied to a surface. The correlation can be optical, acoustical, magnetic, or electromagnetic.

The principles of the invention are invariant of the material.

Figure 7:
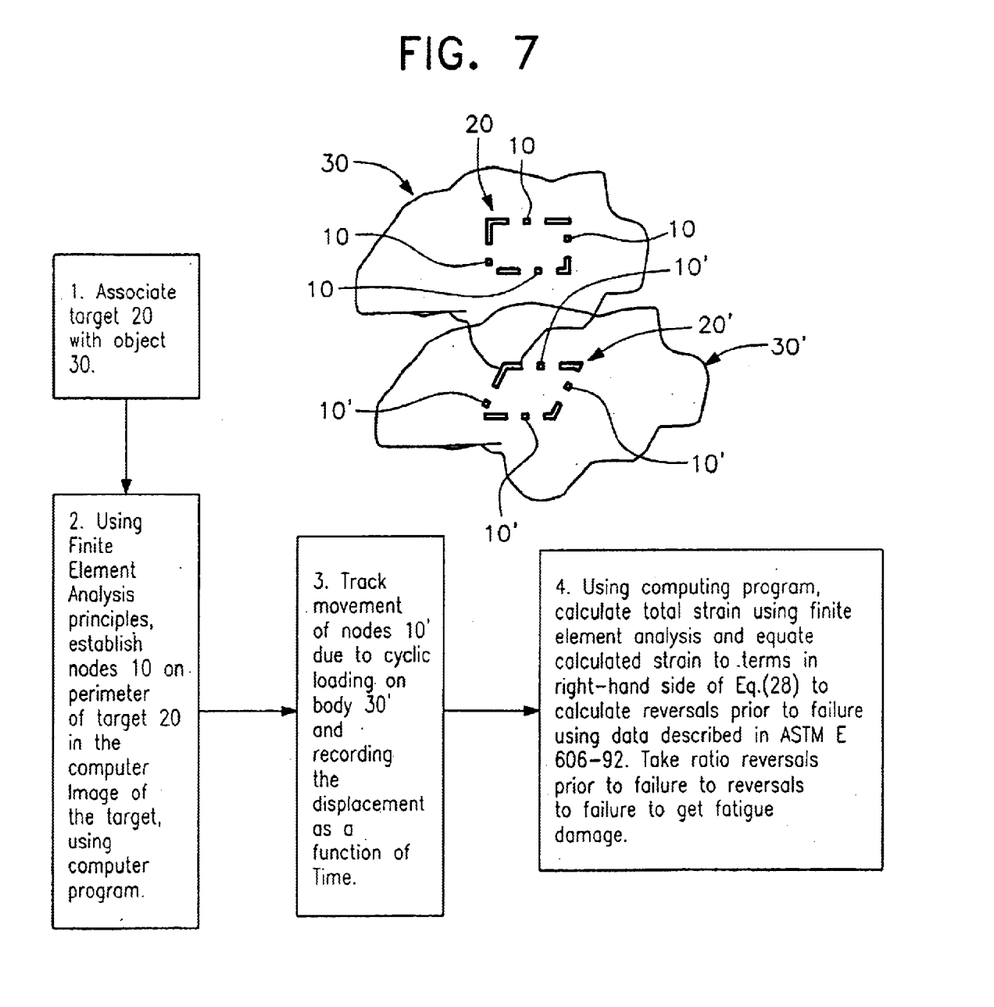
FIG. 7 is a schematic diagram representing the steps in the application of the finite element fatigue gage.

FIG. 7 presents a schematic of the steps in the application of the finite element fatigue gage. The nodes 10 on the perimeter of the target 20 are monitored—by optical, magnetic, electromagnetic, acoustic, or other sensor, as appropriate, as described above—at successive periods of time, either on a continuous time, at random times triggered by an external event, or on a programmed time basis. The sensor observes the deformation of the target 20 by capturing the total image of the target 20 and transmitting it to the computer (in FIG. 7, the deformed target and object are denoted by reference numbers 20' and 30', respectively, and the nodes of the deformed target 20' are denoted by reference number 10').

As the object 30 under study is submitted to loading resulting in strain, the computer implements programs that (1) identify the target and assign nodes to the perimeter and the positional changes of the nodes as a function of time and change in the load, (2) translate the positional changes in the nodes into strain, and (3) display one or both of strain and the resultant fatigue damage in a suitable format. The display of the data can take place in real time. The technology is scalable with respect to the size of the object under study.

The method for calculating strain and fatigue damage in materials in accordance with the present invention comprises the steps of:

1. Associating (for example, by affixing or forming or identifying) a geometric shape on the surface of, or internally to, a body 30 to be subjected to cyclic loading, the geometric shape defining a target 20;
2. Using a sensor (operating in any portion of the electromagnetic or acoustic spectra or a magnetic field) to observe the surface 30 and the target 20;
3. Using a computer program to isolate the perimeter of the target 20 based on data obtained from the sensor;
4. Inputting to a computer program the mechanical properties of the body 30 (monotonic and cyclic);
5. Using the computer program to set the number of nodes 10 to be tracked and establishing the nodes 10 on the perimeter of the target 20 in accordance with finite element theory;
6. Tracking, relative to a coordinate system and as a function of time, the movement of perimeter nodes 10' of the target 20' as the body 30' undergoes deformation during or after the termination of cyclic loading, and recording the displacement as a function of time using the computer program;
7. Utilizing the data on movement of nodes in finite element equations to calculate total strain and then substituting the calculated total to an equation developed for strain as a function of monotonic and cyclic properties and reversals (as described by Stephens et al., or any modification, improvement, or update to the equation described by Stephens et al., or any new or other approach to describe total strain in terms of elastic and plastic strain and monotonic and cyclic properties) to calculate fatigue damage as a function of the local total strain.

Modifications and variations of the above-described embodiments of the present invention are possible, as appreciated by those skilled in the art in light of the above teachings. It is therefore to be understood that, within the scope of the appended claims and their equivalents, the invention may be practiced otherwise than as specifically described.

What is claimed is:

1. Apparatus for calculating strain and fatigue damage in materials based on observing the deformation of a geometric shape associated with a body undergoing cyclic loading, the geometric shape being affixed to or identified on or formed in the surface of the body and defining a target, the target having a perimeter, being associated with the body in such a way that the deformation of the target and the deformation under load of the body with which it is associated bear a one-to-one relationship, and emitting or reflecting a detectable physical quantity, the apparatus comprising:

sensor means for capturing the total image of a target and for outputting data representing the total image of the target, means for isolating the perimeter of the target using edging algorithms and the data acquired from the sensor means, means for setting a number of nodes to be tracked and establishing the nodes on the perimeter of the target in accordance with finite element theory, means for tracking, relative to a coordinate system and as a function of time, the movement of perimeter nodes of the target as the body undergoes deformation during or after the termination of cyclic loading, and recording the displacement as a function of time, means for manipulating the data on movement of the nodes using (i) fundamental concepts of nonlinear stress analysis, (ii) finite element analysis, and (iii) material properties and characteristics and an equation based on strain-controlled test methods, and means for displaying the results of the computer manipulated data.

2. The apparatus of claim 1, wherein the sensor means operates in any portion of at least one of the electromagnetic and acoustic spectra and a magnetic field.

3. The apparatus of claim 1, wherein the sensor means is selected to be compatible with the detectable physical quantity emitted or reflected by the target and undertakes some pre-processing of the observed physical quantity to provide data representing the physical quantity to the computer.

4. The apparatus of claim 1, wherein the sensor means captures data on a continuous basis.

5. The apparatus of claim 1, wherein the sensor means captures data at random times triggered by an external event.

6. The apparatus of claim 1, wherein the sensor means captures data at pre-determined intervals.

7. A method for calculating strain and fatigue damage in materials, the method comprising the steps of:

associating a geometric shape with a body to be subjected to cyclic loading, to define a target, the target having a perimeter, being associated with the body in such a way that the deformation of the target and the deformation under load of the body with which it is associated bear a one-to-one relationship, and emitting or reflecting a detectable physical quantity;

using a sensor to capture the total image of the target;

using a computer program to isolate the perimeter of the target based on data obtained from the sensor;

inputting to a computer program the monotonic and cyclic mechanical properties of the body;

using the computer program to set a number of nodes to be tracked and establishing the nodes on the perimeter of the target in accordance with finite element theory;

tracking, relative to a coordinate system and as a function of time, the movement of perimeter nodes of the target as the body undergoes deformation during or after the termination of cyclic loading, and recording the displacement as a function of time using the computer program; and utilizing the data on movement of the nodes in finite element equations to calculate total strain, and then substituting the calculated total strain into an equation developed for strain as a function of monotonic and cyclic properties and reversals to calculate fatigue damage as measured by the local total strain.

8. The method of claim 7, wherein in said step of using a sensor, the sensor operates in any portion of at least one of the electromagnetic and acoustic spectra and a magnetic field.

9. The method of claim 7, further comprising the step of pre-processing of the observed physical quantity to provide data representing the physical quantity to the computer.

10. The method of claim 7, wherein in said step of using a sensor, the body and the target are observed on a continuous basis.

11. The method of claim 7, wherein in said step of using a sensor, the body and the target are observed at random times triggered by an external event.

12. The method of claim 7, wherein in said step of using a sensor, the body and the target are observed at pre-determined intervals.

* * * * *